United States Patent
Barman et al.

(10) Patent No.: US 11,013,549 B2
(45) Date of Patent: May 25, 2021

(54) GASTROINTESTINAL NEUROMODULATION AND ASSOCIATED SYSTEMS AND METHODS

(71) Applicants: MEDTRONIC ARDIAN LUXEMBOURG SARL, Luxembourg (LU); Neil Barman, Mountain View, CA (US)

(72) Inventors: Neil Barman, Mountain View, CA (US); Ayala Hezi-Yamit, Santa Rosa, CA (US); Stefan Tunev, Santa Rosa, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 671 days.

(21) Appl. No.: 14/379,917

(22) PCT Filed: Mar. 7, 2013

(86) PCT No.: PCT/US2013/029679
§ 371 (c)(1),
(2) Date: Aug. 20, 2014

(87) PCT Pub. No.: WO2013/134541
PCT Pub. Date: Sep. 12, 2013

(65) Prior Publication Data
US 2015/0119867 A1 Apr. 30, 2015

Related U.S. Application Data

(60) Provisional application No. 61/608,631, filed on Mar. 8, 2012.

(51) Int. Cl.
*A61B 18/14* (2006.01)
*A61B 5/00* (2006.01)
(Continued)

(52) U.S. Cl.
CPC ............ *A61B 18/14* (2013.01); *A61B 5/4035* (2013.01); *A61B 5/42* (2013.01); *A61B 18/02* (2013.01);
(Continued)

(58) Field of Classification Search
CPC ........ A61B 18/14; A61B 5/4035; A61B 18/24
(Continued)

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| CN | 103096826 | 5/2013 |
| EP | 0737487 | 10/1996 |

(Continued)

OTHER PUBLICATIONS

Kiba, Relationships Between the Autonomic Nervous System and the Pancreas Including Regulation of Regeneration and Apoptosis, Aug. 2004, Pancreas, vol. 29 No. 2, p. e51-e58.*

(Continued)

*Primary Examiner* — Jonathan T Kuo

(57) ABSTRACT

Methods for treating gastrointestinal conditions, conditions associated with sympathetic and/or parasympathetic activity in the gastrointestinal organs, and conditions associated with central sympathetic and/or parasympathetic activity in a patient with therapeutic gastrointestinalneuromodulation and associated systems and methods are disclosed herein. One aspect of the present technology is directed to methods that at least partially inhibit sympathetic neural activity in nerves proximate a gastrointestinal artery of a gastrointes- (Continued)

tinal organ of a patient. Sympathetic drive in the patient can thereby be reduced in a manner that treats the patient for the gastrointestinal condition.

16 Claims, 6 Drawing Sheets

(51) Int. Cl.
    *A61B 18/02*     (2006.01)
    *A61B 18/18*     (2006.01)
    *A61B 18/20*     (2006.01)
    *A61N 7/00*     (2006.01)
    *A61B 18/00*     (2006.01)
    *A61N 1/36*     (2006.01)
    *A61F 7/12*     (2006.01)
    *A61N 7/02*     (2006.01)
    *A61B 18/24*     (2006.01)
    *A61F 7/00*     (2006.01)

(52) U.S. Cl.
    CPC .......... *A61B 18/1492* (2013.01); *A61B 18/18* (2013.01); *A61B 18/1815* (2013.01); *A61B 18/20* (2013.01); *A61N 7/00* (2013.01); *A61B 18/24* (2013.01); *A61B 2018/0016* (2013.01); *A61B 2018/00214* (2013.01); *A61B 2018/00434* (2013.01); *A61B 2018/00494* (2013.01); *A61B 2018/00577* (2013.01); *A61B 2018/00773* (2013.01); *A61B 2018/00791* (2013.01); *A61B 2018/00839* (2013.01); *A61B 2018/0212* (2013.01); *A61B 2018/1861* (2013.01); *A61F 7/123* (2013.01); *A61F 2007/0056* (2013.01); *A61F 2007/126* (2013.01); *A61N 1/36007* (2013.01); *A61N 7/022* (2013.01); *A61N 2007/003* (2013.01); *A61N 2007/0043* (2013.01)

(58) Field of Classification Search
    USPC .......................... 606/2, 21, 32, 33, 41, 169
    See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,037,391 A | 8/1991 | Hammerslag et al. |
| 5,170,803 A | 12/1992 | Hewson et al. |
| 5,203,772 A | 4/1993 | Hammerslag et al. |
| 5,300,068 A | 4/1994 | Rosar et al. |
| 5,322,064 A | 6/1994 | Lundquist |
| 5,358,514 A | 10/1994 | Schulman et al. |
| 5,368,591 A | 11/1994 | Lennox et al. |
| 5,415,633 A | 5/1995 | Lazarus et al. |
| 5,423,744 A | 6/1995 | Gencheff et al. |
| 5,425,364 A | 6/1995 | Imran |
| 5,437,288 A | 8/1995 | Schwartz et al. |
| 5,484,400 A | 1/1996 | Edwards et al. |
| 5,487,757 A | 1/1996 | Truckai et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,662,699 A * | 9/1997 | Hamedi ............... A61N 1/0524 607/138 |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,766,167 A | 6/1998 | Eggers et al. |
| 5,772,590 A | 6/1998 | Webster, Jr. |
| 5,843,152 A | 12/1998 | Tu et al. |
| 5,860,974 A | 1/1999 | Abele |
| 5,865,787 A | 2/1999 | Shapland et al. |
| 5,893,885 A | 4/1999 | Webster et al. |
| 5,899,898 A | 5/1999 | Arless et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,106,518 A | 8/2000 | Wittenberger et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,425,867 B1 | 7/2002 | Vaezy et al. |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,887,235 B2 | 5/2005 | O'Connor et al. |
| 6,893,436 B2 | 5/2005 | Woodard et al. |
| 6,939,346 B2 | 9/2005 | Kannenberg et al. |
| 6,978,174 B2 | 12/2005 | Gelfand et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,728,075 B2 | 5/2014 | Wu et al. |
| 9,486,243 B2 | 11/2016 | Eskuri |
| 2002/0065542 A1 | 5/2002 | Lax et al. |

(56) References Cited

U.S. PATENT DOCUMENTS

| | | |
|---|---|---|
| 2002/0087208 A1 | 7/2002 | Koblish et al. |
| 2002/0107515 A1 | 8/2002 | Edwards et al. |
| 2002/0128662 A1 | 9/2002 | Brock et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2002/0198520 A1 | 12/2002 | Coen et al. |
| 2003/0050635 A1 | 3/2003 | Truckai et al. |
| 2003/0050681 A1 | 3/2003 | Pianca et al. |
| 2003/0055422 A1 | 3/2003 | Lesh |
| 2003/0060858 A1 | 3/2003 | Kieval et al. |
| 2003/0074039 A1 | 4/2003 | Puskas |
| 2003/0109778 A1 | 6/2003 | Rashidi |
| 2003/0125720 A1 | 7/2003 | Woodard et al. |
| 2003/0125790 A1 | 7/2003 | Fastovsky et al. |
| 2003/0181897 A1 | 9/2003 | Thomas et al. |
| 2003/0181958 A1* | 9/2003 | Dobak, III .......... A61N 1/36085 607/58 |
| 2003/0199863 A1 | 10/2003 | Swanson et al. |
| 2003/0212394 A1 | 11/2003 | Pearson et al. |
| 2003/0216792 A1 | 11/2003 | Levin et al. |
| 2003/0229340 A1 | 12/2003 | Sherry et al. |
| 2004/0010289 A1 | 1/2004 | Biggs et al. |
| 2004/0073141 A1 | 4/2004 | Hartley et al. |
| 2004/0215186 A1 | 10/2004 | Cornelius et al. |
| 2005/0004644 A1 | 1/2005 | Kelsch et al. |
| 2005/0021092 A1* | 1/2005 | Yun .................... A61N 1/326 607/3 |
| 2005/0080409 A1 | 4/2005 | Young et al. |
| 2005/0096647 A1 | 5/2005 | Steinke et al. |
| 2005/0187455 A1 | 8/2005 | Rashidi |
| 2005/0187579 A1 | 8/2005 | Danek et al. |
| 2005/0228460 A1 | 10/2005 | Levin et al. |
| 2005/0267010 A1 | 12/2005 | Goodson et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0271111 A1 | 11/2006 | Demarais et al. |
| 2007/0093870 A1* | 4/2007 | Maschino .......... A61N 1/36085 607/2 |
| 2007/0129720 A1 | 6/2007 | Demarai et al. |
| 2007/0156131 A1 | 7/2007 | Datta |
| 2007/0265687 A1 | 11/2007 | Deem et al. |
| 2008/0255642 A1 | 10/2008 | Zarins et al. |
| 2008/0319513 A1 | 12/2008 | Pu et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0268297 A1 | 10/2010 | Neisz |
| 2010/0286684 A1 | 11/2010 | Hata et al. |
| 2011/0029030 A1 | 2/2011 | Yun et al. |
| 2011/0029037 A1 | 2/2011 | Rezai et al. |
| 2011/0264075 A1 | 10/2011 | Leung et al. |
| 2012/0116382 A1 | 5/2012 | Ku et al. |
| 2012/0130289 A1 | 5/2012 | Demarais et al. |
| 2012/0130345 A1 | 5/2012 | Levin et al. |
| 2012/0136350 A1 | 5/2012 | Goshgarian et al. |
| 2012/0150267 A1 | 6/2012 | Buckley et al. |
| 2012/0172837 A1 | 7/2012 | Demarais et al. |
| 2014/0066923 A1 | 3/2014 | Azamian et al. |
| 2015/0190634 A1 | 7/2015 | Rezai et al. |

FOREIGN PATENT DOCUMENTS

| | | |
|---|---|---|
| EP | 2563255 | 3/2013 |
| WO | WO-199407446 | 4/1994 |
| WO | WO-1995025472 | 9/1995 |
| WO | WO-9531142 | 11/1995 |
| WO | WO-1997036548 | 10/1997 |
| WO | WO1998042403 | 10/1998 |
| WO | WO-1999/00060 | 1/1999 |
| WO | WO-9900060 | 1/1999 |
| WO | WO1999000060 | 1/1999 |
| WO | WO-2001022897 | 4/2001 |
| WO | WO-2001070114 | 9/2001 |
| WO | WO-2003022167 | 3/2003 |
| WO | WO-2003/082080 | 10/2003 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO2006086152 | 8/2006 |
| WO | WO-2006105121 A2 | 10/2006 |
| WO | WO-2007008954 | 1/2007 |
| WO | WO-2007078997 A2 | 7/2007 |
| WO | WO-2008049084 A2 | 4/2008 |
| WO | WO2009086007 | 7/2009 |
| WO | WO2011139589 | 11/2011 |
| WO | WO2012054906 | 4/2012 |
| WO | WO-2013134541 | 9/2013 |

OTHER PUBLICATIONS

Mundinger et al., Direct Stimulation of Ghrelin Secretion by Sympathetic Nerves, Mar. 9, 2006, Endocrinology, 147(6):2893-2901, doi: 10.1210/en.2005-1182.*

Poitras and Peeters, Motilin, 2008, Current Opinion in Endocrinology, Diabetes & Obesity 2008, 15:54-57.*

Mancia et al., The sympathetic nervous system and the metabolic syndrome, 2007, Journal of Hypertension 2007, 25:909-920.*

Barry, Danielle, Megan Clarke, and Nancy M. Petry. "Obesity and its relationship to addictions: is overeating a form of addictive behavior?." The American Journal on Addictions 18.6 (2009): 439-451. doi: 10.3109/10550490903205579.*

Mahfoud, Felix, et al. "Effect of renal sympathetic denervation on glucose metabolism in patients with resistant hypertensionClinical perspective: a Pilot study." Circulation 123.18 (2011): 1940-1946. doi: 10.1161/CIRCULATIONAHA.110.991869.*

Thorp, Alicia A., and Markus P. Schlaich. "Relevance of sympathetic nervous system activation in obesity and metabolic syndrome." Journal of diabetes research 2015 (2015). doi: 10.1155/2015/341583.*

Insulin—Oxford Dictionary of Biology Reference.*

European Search Report for European Application No. 13159256, dated Oct. 17, 2013, 6 pages.

U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.

(56) References Cited

OTHER PUBLICATIONS

"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards [TM]" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Intery Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.
Gelfand, M., et al., "Treatment of renal failure and hypertension." U.S. Appl. No. 60/442,970, Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).

(56) References Cited

OTHER PUBLICATIONS

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversible renal denervation on haemodynamic and excretory functions on the ipsilateral and contralateral kidney in the cat." Hypertension, 4:181-188 (1986).

Stouffer, G. A. et al., "Catheter-based renal denervation in the treatment of resistant hypertension." Journal of Molecular and Cellular Cardiology, vol. 62, 2013, 6 pages.

Swartz, J.F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Weinstock, M., et al., "Renal denervation prevents sodium retention and hypertension in salt sensitive rabbits with genetic baroreflex impairment." Clinical Science, 90:287-293 (1996).

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Miller, Reed, "Finding a Future for Renal Denervation With Better Controlled Trials." Pharma & Medtech Business Intelligence, Article # 01141006003, Oct. 6, 2014, 4 pages.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter, "Journal of the American College of Cardiology, 1999; 33; pp. 972-984.

Beale et al., "Minimally Invasive Treatment for Varicose Veins: A Review of Endovenous Laser Treatment and Radiofrequency Ablation". Lower Extremity Wounds 3(4), 2004, 10 pages.

Blessing, Erwin et al., Cardiac Ablation and Renal Denervation Systems Have Distinct Purposes and Different Technical Requirements, JADD Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Opposition to European Patent No. EP2092957, Granted Jan. 5, 2011, Date of Opposition Oct. 5, 2011, 26 pages.

Oz, Mehmet, Pressure Relief, TIME, Jan. 9, 2012, 2 pages. <www.time.come/time/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20 :484-490, 2005.

(56) References Cited

OTHER PUBLICATIONS

Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Pieper et al., "Design and Implementation of a New Computerized System for Intraoperative Cardiac Mapping." Journal of Applied Physiology, 1991, vol. 71, No. 4, pp. 1529-1539.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
U.S. Appl. No. 60/852,787, filed Oct. 18, 2006, 112 pages.
International Search Report and Written Opinion for International App. No. PCT/US2013/029679, dated May 8, 2013, 8 pages.
Orshoven, N., et al., "Subtle involvement of the parasympathetic nervous system in patients with irritable bowel syndrome." Clin Auton Res (2006) 16: 33-39.
Kiba et al., "Relationships Between the Autonomic Nervous System and the Pancreas Including Regulation of Regeneration and Apoptosis," Aug. 2004, Pancreas, vol. 29, No. 2, p. e51-e58.
Poitras et al., Motilin, 2008, Current Opinion in Endocrinology, Diabetes & Obesity 2008, 15:54-57.
Batterham et al., "Pancreatic polypeptide reduces appetite and food intake in humans," J Clin Endocrinol Metab, Aug. 2003, 88(8):3989-3992.
Tschop et al., "Circulating Ghrelin Levels Are Decreased in Human Obesity," Diabetes, Apr. 2001, vol. 50, pp. 707-709.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Barbieri, et al., "Treatment of polycystic ovary syndrome in adults," Wolters Kluwer Health, 2012, 11 pgs. <http://www.uptodate.com>.
Barria, et al., "Ovarian Steroidal Response to Gonadotropins and β-Adrenergic Stimulation Is Enhanced in Polycystic Ovary Syndrome: Role of Sympathetic Innervation." Endocrinology, 1993, vol. 133, No. 6, 8 pages.
Diamanti-Kandarakis, et al., "The Role of Genes and Environment in the Etiology of PCOS." Endocrine, vol. 30, No. 1, Aug. 2006, pp. 19-26.
Ehrmann, "Polycystic Ovary Syndrome," The New England Journal of Medicine, vol. 352, 2005, 1223-36.
Esler, et al., "Catheter-Based Renal Denervation Reduces Total Body and Renal Noradrenaline Spillover and Blood Pressure in Resistant," Hypertension, J Hypertens vol. 27, 2009, 1 page.
Fauser, et al. "Consensus on women's health aspects of polycystic ovary syndrome (PCOS): the Amsterdam ESHRE/ASRM-Sponsored 3rd PCOS Consensus Workshop Group." Fertility and sterility 2012; 97: 36 pages.
Hendriks, et al. "Why does ovarian surgery in PCOS help? Insight into the endocrine implications of ovarian surgery for ovulation induction in polycystic ovary syndrome." Human reproduction update, 2007; 13: 16 pages.
Himelein, et al. "Polycystic ovary syndrome and mental health: A review." Obstet Gynecol. Surv. 2006; 61(11): 723-732.

(56) References Cited

OTHER PUBLICATIONS

Lansdown, et al. "The Sympathetic Nervous System in Polycystic Ovary Syndrome: a novel therapeutic target?" Clinical endocrinology, 2012, 28 pages.

Lara, et al., "Activation of ovarian sympathetic nerves in polycystic ovary syndrome." Endocrinology 1993; 133, 6 pages.

Lembo, et al., "A Lesson from Polycystic Ovarian Syndrome: Untangling the Role of Renal Sympathetic Nervous System on Hypertension and Insulin Resistance", Journal of Hypertension, 2011, vol. 29 (5), pp. 836-837.

Nakamura, "Treatment of Polycystic Ovary Syndrome: An Overview." Hormone Research 1990; 33: 1 page.

Opposition to European U.S. Pat. No. 2465470, Granted Oct. 28, 2015, Date of Opposition Jul. 27, 2016, 34 pp.

Schlaich, et al., "Renal denervation: a potential new treatment modality for polycystic ovary syndrome?" J Hypertens 2011; 29: 991-6.

Schlaich, et al., "A Novel Catheter Based Approach to Denervate the Human Kidney Reduces Blood Pressure and Muscle Sympathetic Nerve Activity in a Patient with End Stage Renal Disease and Hypertension." J Hypertens 2009; 27: 1 page.

Schlaich, et al., Renal sympathetic-nerve ablation for uncontrolled hypertension. N Engl J Med 2009; 361: 932-4.

Search Report and Written Opinion dated Apr. 23, 2012 for PCT Application No. PCT/US2011/057402.

Search Report and Written Opinion dated Nov. 22, 2011 for PCT Application No. PCT/US2011/033491.

Stener-Victorin, et al., "Acupuncture in Polycystic Ovary Syndrome: Current Experimental and Clinical Evidence", J. Neuroendocrinol, 2008, vol. 20 (3), pp. 290-298.

Stener-Victorin, et al. "Low-frequency electroacupuncture and physical exercise decrease high muscle sympathetic nerve activity in polycystic ovary syndrome." Am J Physiol Regul Integr Comp Physiol, 2009; 297: R387-95.

Sverrisdottir, et al., "Is Polycystic Ovary Syndrome Associated with High Sympathetic Nerve Activity and Size at Birth?" American Journal of Physiology—Endocrinology and Metabolism. Jan. 15, 2008, vol. 294, p. E576-E581.

Ureter, https://en.wikipedia.org/wiki/Ureter, Jun. 2016, 6 pgs.

Valente, et al., "Laparoscopic renal denevation for intractable ADPKD-related pain." Nephrol Dial Transplant, 2001, 16, 160, 1 page.

\* cited by examiner

GASTROINTESTINAL NEUROMODULATION AND ASSOCIATED SYSTEMS AND METHODS

RELATED APPLICATIONS

The present application claims the benefit of International Patent Application No. PCT/US2013/029679, filed Mar. 7, 2013, entitled "GASTROINTESTINAL NEUROMODULATION AND ASSOCIATED SYSTEMS AND METHODS," which claims the benefit of U.S. Provisional Patent Application No. 61/608,631, filed Mar. 8, 2012, entitled "GASTROINTESTINAL NEUROMODULATION AND ASSOCIATED SYSTEMS AND METHODS," both of which are incorporated herein by reference in their entireties.

TECHNICAL FIELD

The present technology relates generally to modulation of gastrointestinal nerves and associated systems and methods.

BACKGROUND

The sympathetic nervous system (SNS) is a primarily involuntary bodily control system typically associated with stress responses. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. Signals sent via these and other fibers can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
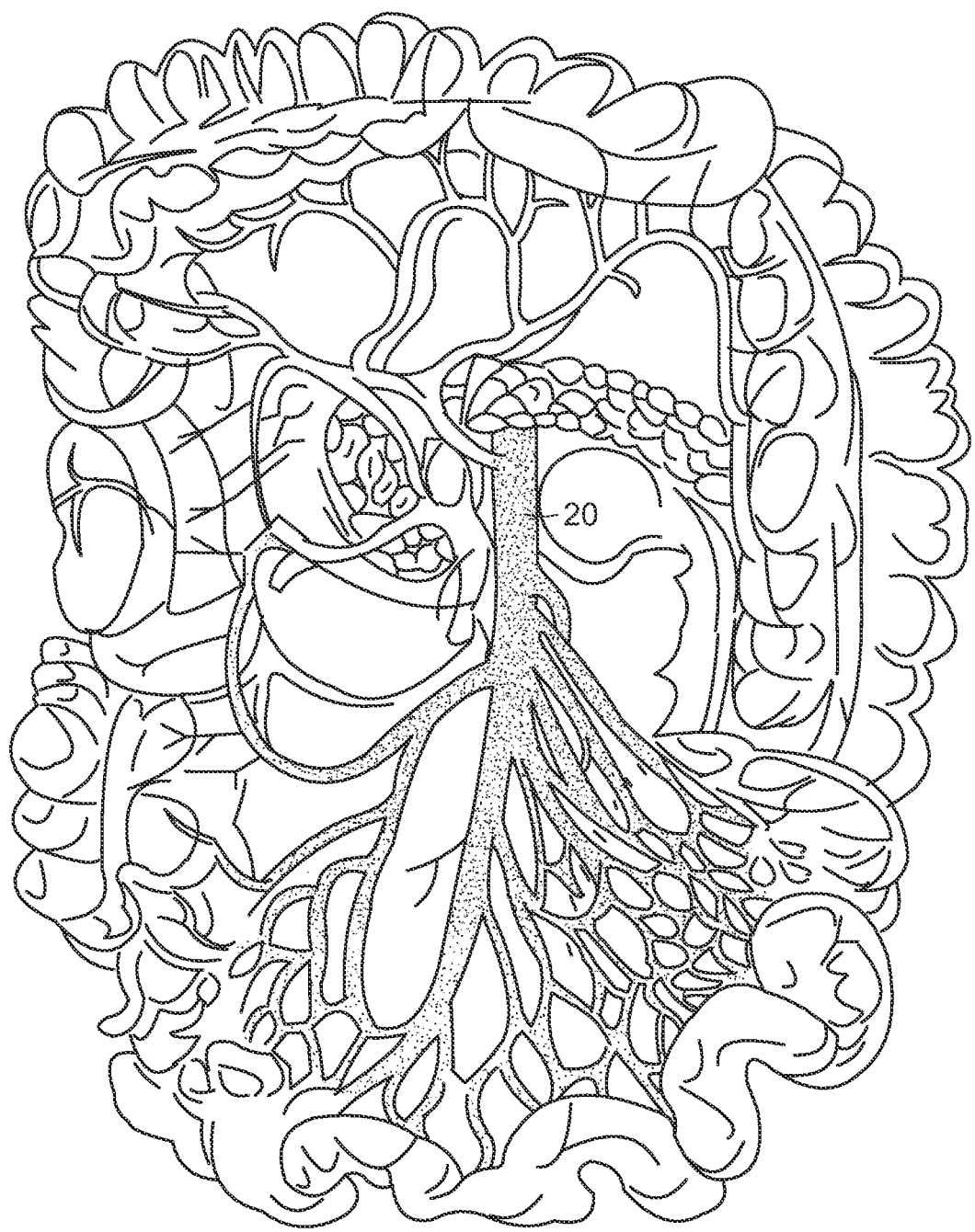
FIG. 1A is an anatomical view illustrating the superior mesenteric artery and nearby organs and vessels.

The present technology is generally directed to modulation of nerves of one or more gastrointestinal organs to treat gastrointestinal conditions, conditions associated with imbalances of sympathetic and/or parasympathetic activity (e.g., overactivity or hyperactivity of the sympathetic nervous system and/or hypoactivity of the parasympathetic nervous system) in the gastrointestinal organs, and/or conditions associated with imbalances in central sympathetic and/or parasympathetic activity. For example, several embodiments are directed to modulation of nerves of one or more gastrointestinal organs to treat inflammatory bowel disease and related conditions. As discussed in greater detail below, gastrointestinal neuromodulation can include rendering neural fibers inert, inactive, or otherwise completely or partially reduced in function. This result can be electrically-induced, thermally-induced, chemically-induced, or induced by another mechanism during a gastrointestinal neuromodulation procedure.

Specific details of several embodiments of the present technology are described herein with reference to FIGS. 1A-3. The embodiments can include, for example, modulating nerves proximate (e.g., at or near) the superior mesenteric artery, the inferior mesenteric artery, the superior mesenteric vein, the inferior mesenteric vein, another portion of a vessel or duct of a gastrointestinal organ, and/or other suitable structures. Although many of the embodiments are described herein with respect to electrically-induced, thermally-induced, and chemically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1A-3.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. Inflammatory Bowel Disease and Gastric Motility Disorders

Inflammatory bowel disease (IBD) includes, among other things, Crohn's disease, ulcerative colitis, collagenous colitis, lymphocytic colitis, ischaemic colitis, diversion colitis, and Behcet's disease. Of these, Crohn's disease and ulcerative colitis are the most common. The precise cause of these conditions is unknown. They can be distinguished from one another by differences in genetic predisposition, risk factors, and clinical, endoscopic, and histological features. However, they also share certain features. For example, many genetically susceptible individuals have a dysregulated mucosal immune response to commensal gut flora, resulting in bowel inflammation. In addition to genetic predisposition and certain environmental triggers, subjects with IBD tend to share common immune and inflammatory responses.

Common symptoms of IBD include abdominal pain, vomiting, diarrhea, bleeding in the gastrointestinal tract, severe internal cramps/muscle spasms in the region of the pelvis, and weight loss. Other associated conditions include anemia, arthritis, pyoderma gangrenosum, and primary sclerosing cholangitis. IBD is generally treated with medications that alter the gastrointestinal mucosa or systemically modify the immune system. In certain cases, surgery is also an option. Current treatment options, however, have a number of drawbacks including the occurrence of acute disease flares despite treatment and the requirement for regular (e.g., daily) medication for long periods of time and, in many cases, for the rest of a patient's life.

In normal digestion, rhythmic contractions called peristalsis function to move food through the digestive tract. In patients with gastric motility disorders, peristalsis is abnormal due to problems with the nerves or hormones that control muscle contraction or with the muscles themselves. The most common gastric motility disorder is irritable bowel syndrome (IBS), symptoms of which include abdominal pain, diarrhea, and constipation.

II. Gastrointestinal Neuromodulation

Gastrointestinal neuromodulation is the partial or complete incapacitation or other effective disruption or regulation of gastrointestinal nerves, e.g., nerves terminating in or originating from one or more gastrointestinal organs (including, but not limited to the stomach, small intestine, large intestine, pancreas, gut-associated lymphoid tissue (GALT), and other suitable organs) or in structures closely associated with the gastrointestinal organs. In particular, gastrointestinal neuromodulation comprises inhibiting, reducing, blocking, pacing, upregulating, and/or downregulating neural communication along neural fibers efferent and/or afferent neural fibers) innervating one or more gastrointestinal organs. Such incapacitation, disruption, and/or regulation can be long-term (e.g., permanent or for periods of months, years, or decades) or short-term (e.g., for periods of minutes, hours, days, or weeks). While long-term disruption of the gastrointestinal nerves can be desirable for alleviating symptoms and other sequelae associated with IBD, gastric motility disorders, and other gastrointestinal conditions over longer periods of time, short-term modulation of the gastrointestinal nerves may also be desirable, for example, to generate a temporary reduction in symptoms or to address other issues.

Gastrointestinal sympathetic and/or parasympathetic neural activity can cause or exacerbate various gastrointestinal conditions, including for example IBD, gastric motility disorders, maldigestion, other chronic inflammatory diseases of the gastrointestinal tract, and other gastrointestinal conditions. Further, gastrointestinal sympathetic and/or parasympathetic activity may also be relatively high in patients who are obese and/or have an overeating condition. Gastrointestinal neuromodulation is expected to be useful in treating these conditions, for example by reducing mechanisms of inflammation, modulating the immune response, and/or relaxing the gastrointestinal vasculature. Circumstantial evidence for the influence of the sympathetic nervous system on IBD can be seen in the widely reported link between stressful life events and disease flares. In addition, animal models of colitis have shown increased nerve firing in the mesenteric ganglia, suggesting that sympathetic nerve traffic is important in disease pathophysiology. The disclosed methods and systems for gastrointestinal neuromodulation are expected to efficaciously treat several clinical conditions characterized by increased gastrointestinal sympathetic or parasympathetic activity, including IBD, gastric motility disorders, and other gastrointestinal conditions, obesity, overeating, and associated conditions such as hypertension.

Furthermore, afferent nerve activity from gastrointestinal organs can contribute to central sympathetic and/or parasympathetic tone or drive. Accordingly, gastrointestinal neuromodulation is expected to be useful in treating clinical conditions associated with central sympathetic and/or parasympathetic activity (e.g., overactivity or hyperactivity), particularly conditions associated with central sympathetic and/or parasympathetic overstimulation. Conditions associated with central sympathetic and/or parasympathetic activity (e.g., overactivity or hyperactivity) include, for example, hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

By way of theory, targeting both afferent and efferent gastrointestinal nerves (e.g., via a catheter-based approach) may cause beneficial effects extending well beyond the gastrointestinal system and other systemic sequelae of gastrointestinal conditions, such as increased cardiovascular risk. The role of sympathetic activation for blood pressure regulation is well established, as is the relevance of increased renal sympathetic nerve activity for the alterations in renal blood flow and glomerular filtration rate. There is now also clear evidence that sympathetic activation results in adverse consequences on metabolic control, including insulin sensitivity. Additionally, overactivity of the sympathetic nervous system is implicated in the specific etiology of IBD and other gastrointestinal conditions. Some aspects of methods of treating IBD and other gastrointestinal conditions using gastrointestinal neuromodulation are at least in part derived from the recognition described herein that gastrointestinal nerves may contribute to elevated central sympathetic drive.

In certain patients, correcting an imbalance of sympathetic and/or parasympathetic drive in one or more gastrointestinal organs, reducing an imbalance of central sympathetic and/or parasympathetic drive, and/or other benefits from gastrointestinal neuromodulation are expected to outweigh the complete or partial loss of sympathetic- and/or parasympathetic nerve functionality in treated gastrointestinal organs.

Several properties of the gastrointestinal vasculature may inform the design of treatment devices and associated methods for achieving gastrointestinal neuromodulation (e.g., via intravascular access), and impose specific design requirements for such devices. Specific design requirements may include accessing the gastrointestinal blood vessels (e.g., mesenteric arteries or veins), facilitating stable contact between the energy delivery elements of such devices and a luminal surface or wall of the gastrointestinal blood vessel, and/or effectively modulating the gastrointestinal nerves with the neuromodulatory apparatus.

A. Selected Examples of Neuromodulation Modalities

Various techniques can be used to partially or completely incapacitate neural pathways such as those innervating the gastrointestinal organs. Gastrointestinal neuromodulation in accordance with embodiments of the present technology, for example, can be electrically-induced, thermally-induced, chemically-induced, or induced in another suitable manner or combination of manners at one or more suitable treatment locations during a treatment procedure. For example, the purposeful application of radio frequency (RF) energy (monopolar and/or bipolar), pulsed. RF energy, microwave energy, optical energy, ultrasound energy (e.g., intravascularly delivered ultrasound, extracorporeal ultrasound, high-intensity focused ultrasound (HIFU)), magnetic energy, direct heat, cryotherapeutic energy, chemicals (e.g., drugs or other agents), or combinations thereof to tissue at a treatment location can induce one or more desired effects at the treatment location, e.g., broadly across the treatment location or at localized regions of the treatment location.

Figure 2A:
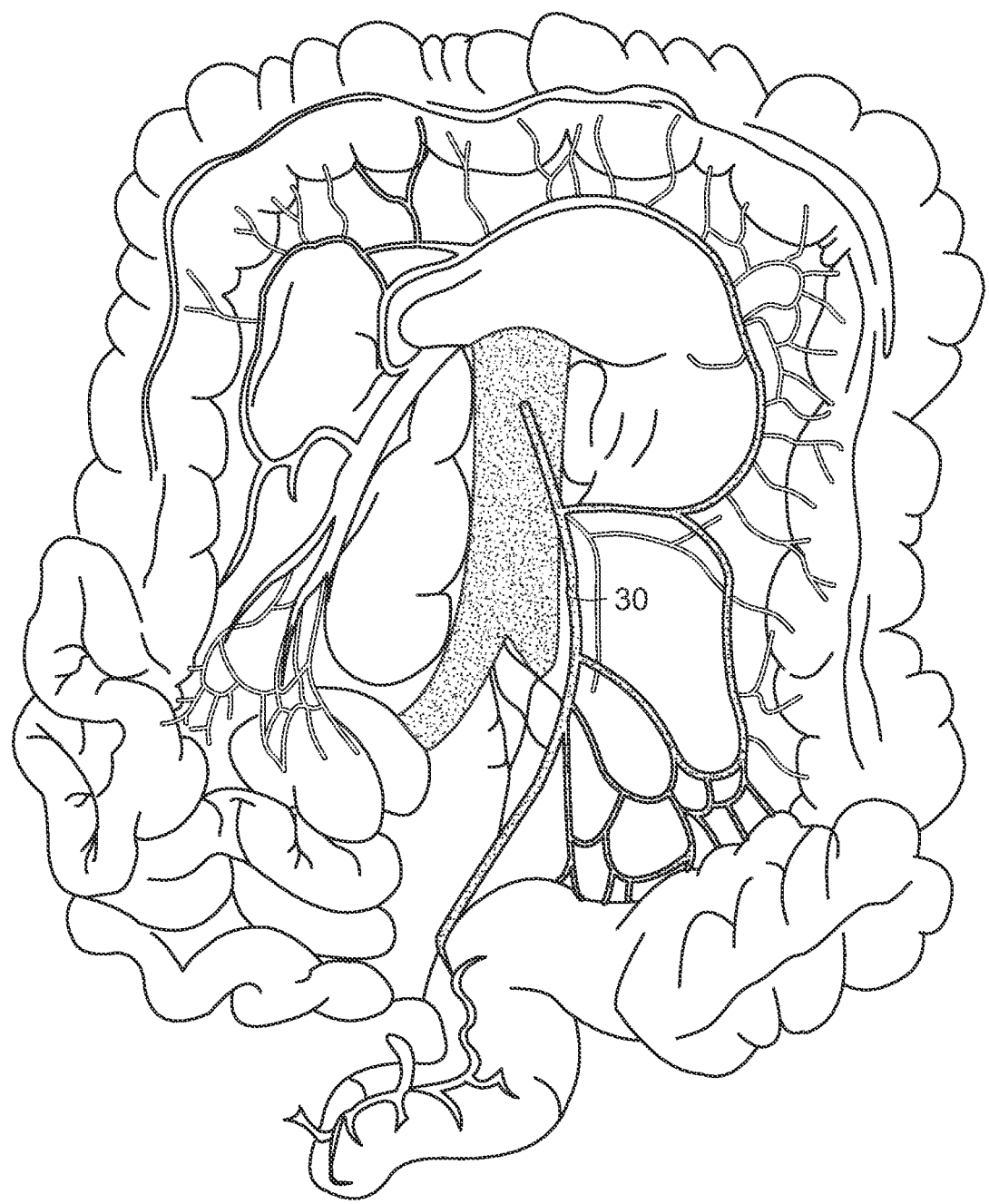
FIG. 2A is an anatomical view illustrating the inferior mesenteric artery and nearby organs and vessels.

FIG. 1A is an anatomical view illustrating a superior mesenteric artery 20 and nearby organs and vessels. FIG. 2A is an anatomical view illustrating an inferior mesenteric artery 30 and nearby organs and vessels. Referring to FIGS. 1A and 2A together, treatment procedures in accordance with embodiments of the present technology can include applying a treatment modality at one or more treatment locations proximate a structure having a relatively high concentration of gastrointestinal nerves. In some embodiments, for example, the treatment locations can be proximate portions of the superior mesenteric artery 20, an ostium of the superior mesenteric artery 20, a branch of the superior mesenteric artery 20, the inferior mesenteric artery 30, an ostium of the inferior mesenteric artery 30, a branch of the inferior mesenteric artery 30, the superior mesenteric vein, an ostium of the superior mesenteric vein, a branch of the superior mesenteric vein, the inferior mesenteric vein, an ostium of the inferior mesenteric vein, a branch of the inferior mesenteric vein, another portion of a vessel or duct of a gastrointestinal organ, and/or another suitable structure.

Figure 1B:
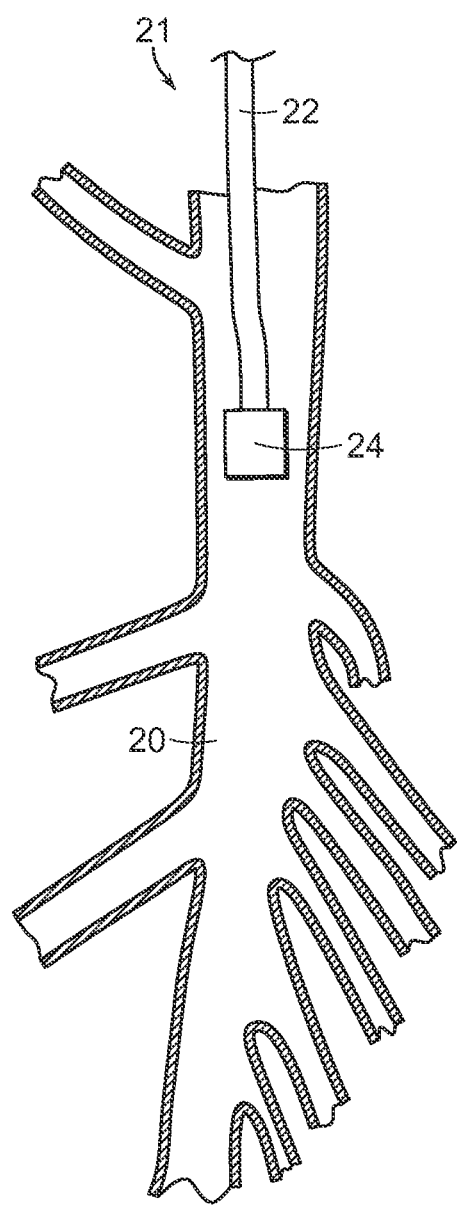
FIG. 1B is a partially cross-sectional view illustrating neuromodulation at a treatment location within the superior mesenteric artery in accordance with an embodiment of the present technology.
Figure 2B:
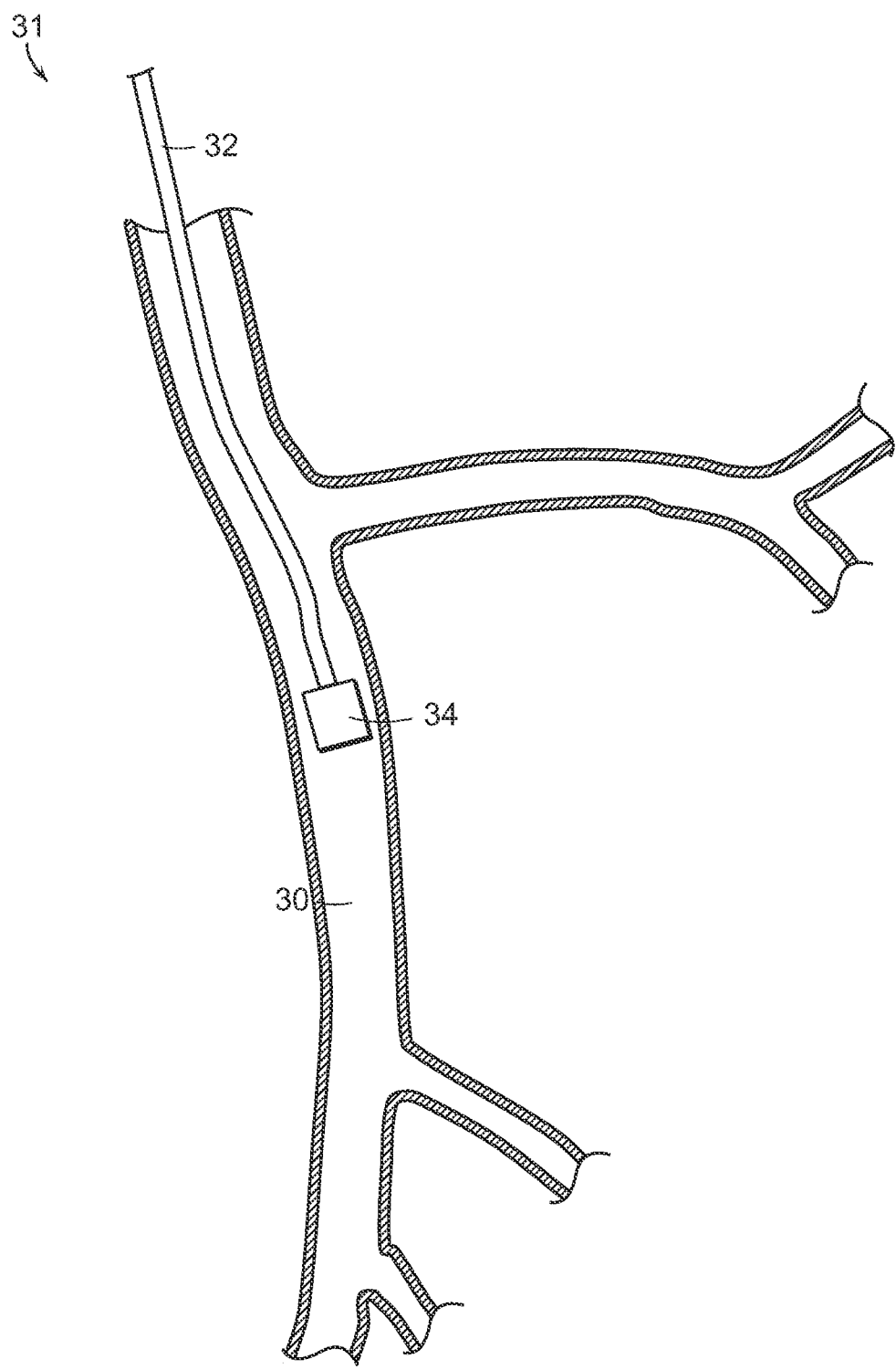
FIG. 2B is a partially cross-sectional view illustrating neuromodulation at a treatment location within the inferior mesenteric artery in accordance with an embodiment of the present technology.

FIGS. 1B and 2B, for example, are cross-sectional views illustrating, respectively, neuromodulation at treatment locations within the superior mesenteric artery 20 and the inferior mesenteric artery 30. As shown in FIG. 1B, a treatment device 21 including a shaft 22 and a therapeutic element 24 can be extended toward the superior mesenteric artery 20 to locate the therapeutic element 24 at a treatment location within the superior mesenteric artery 20. Similarly, as shown in FIG. 2B, a treatment device 31 can be extended toward the inferior mesenteric artery 30 to locate the therapeutic element 34 at a treatment location within the inferior mesenteric artery 30. The therapeutic element 24 or 34 can be configured for neuromodulation at the treatment locations via a suitable treatment modality, e.g., cryotherapeutic, direct heat, electrode-based, transducer-based, chemical-based, or another suitable treatment modality.

The treatment location can be proximate (e.g., at or near) a vessel or duct wall (e.g., a wall of the superior mesenteric artery, the inferior mesenteric artery, the superior mesenteric vein, the inferior mesenteric vein, another portion of a vessel or duct of a gastrointestinal organ, and/or another suitable structure), and the treated tissue can include tissue proximate the treatment location. For example, with regard to the superior mesenteric artery 20 and inferior mesenteric artery 30, respectively, a treatment procedure can include modulating nerves in the superior and inferior mesenteric plexus, which lay at least partially within or adjacent to the adventitia of the superior and inferior mesenteric arteries. In some embodiments it may be desirable to modulate gastrointestinal nerves from a treatment location within a vessel and in close proximity to a gastrointestinal organ, e.g., closer to the gastrointestinal organ than to a trunk of the vessel. This can increase the likelihood of modulating nerves specific to the gastrointestinal organ, while decreasing the likelihood of modulating nerves that extend to other organs. Vessels can decrease in diameter and become more tortuous as they extend toward a gastrointestinal organ. Accordingly, modulating gastrointestinal nerves from a treatment location in close proximity to a gastrointestinal organ can include using a device (e.g., treatment device 21 or 31) having size, flexibility, torque-ability, kink resistance, and/or other characteristics suitable for accessing narrow and/or tortuous portions of vessels.

In some embodiments, the purposeful application of energy (e.g., electrical energy, thermal energy, etc.) to tissue can induce one or more desired thermal heating and/or cooling effects on localized regions of the superior and inferior mesenteric arteries, for example, and adjacent regions along all or a portion of the superior or inferior mesenteric plexus, which lay at least partially within or adjacent to the adventitia of the superior and inferior mesenteric arteries. Some embodiments of the present technology, for example, include cryotherapeutic gastrointestinal neuromodulation (alone or in combination with another treatment modality), which can include cooling tissue at a treatment location in a manner that modulates neural function. For example, sufficiently cooling at least a portion of a sympathetic and/or parasympathetic nerve can slow or potentially block conduction of neural signals to produce a prolonged or permanent reduction in sympathetic and/or parasympathetic activity. The mechanisms of cryotherapeutic tissue damage include, for example, direct cell injury (e.g., necrosis), vascular injury (e.g., starving the cell of nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Several embodiments of the present technology include cooling a structure at or near an inner surface of a vessel or duct wall such that proximate (e.g., adjacent) tissue is effectively cooled to a depth where sympathetic and/or parasympathetic nerves reside. For example, a cooling structure can be cooled to the extent that it causes therapeutically effective cryogenic gastrointestinal neuromodulation. Sufficiently cooling at least a portion of a sympathetic or parasympathetic gastrointestinal nerve may slow or potentially block conduction of neural signals to produce a prolonged or permanent reduction in gastrointestinal sympathetic or parasympathetic activity. In some embodiments, a cryotherapeutic treatment modality can include cooling that is not configured to cause neuromodulation. For example, the cooling can be at or above cryogenic temperatures and can be used to control neuromodulation via another treatment modality, e.g., to reduce damage to non-targeted tissue when targeted tissue adjacent to the non-targeted tissue is heated.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel or duct stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause the gastrointestinal organs to rise and fall and thereby move their associated vessels and ducts. In addition, blood flow is pulsatile and can cause structures to pulse. Cryogenic adhesion also can facilitate intravascular and intraluminal positioning, particularly in relatively small structures (e.g., relatively short arteries) in which stable positioning can be difficult to achieve.

As an alternative to or in conjunction with cryotherapeutic cooling, other suitable energy delivery techniques, such as electrode-based or transducer-based approaches, can be used for therapeutically-effective gastrointestinal neuromodulation. Electrode-based or transducer-based treatment, for example, can include delivering electrical energy and/or another form of energy to tissue and/or heating tissue at a treatment location in a manner that modulates neural function. For example, sufficiently stimulating and/or heating at least a portion of a sympathetic and/or parasympathetic gastrointestinal nerve can slow or potentially block conduction of neural signals to produce a prolonged or permanent reduction in sympathetic and/or parasympathetic activity. As noted previously, suitable energy modalities can include, for example, RF energy (monopolar and/or bipolar), pulsed RF energy, microwave energy, ultrasound energy (e.g., intravascularly delivered ultrasound, extracorporeal ultrasound, HIFU), laser energy, optical energy, magnetic energy, direct heat, or other suitable energy modalities alone or in combination. Where a system uses a monopolar configuration, a return electrode or ground patch fixed externally on the subject can be used. Moreover, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and incorporated herein by reference in its entirety. Other suitable devices and technologies, such as cryotherapeutic devices, are described in U.S. patent application Ser. No. 13/279,330, filed Oct. 23, 2011, and additional thermal devices are described in U.S. patent application Ser. No. 13/279,205, filed Oct. 21, 2011, each of which are incorporated herein by reference in their entireties.

Thermal effects can include both thermal ablation and non-ablative thermal alteration or damage (e.g., via sustained heating and/or resistive heating) to partially or completely disrupt the ability of a nerve to transmit a signal. Desired thermal heating effects may include, for example, raising the temperature of target neural fibers to a target temperature to achieve non-ablative thermal alteration, or to or above a higher target temperature to achieve ablative thermal alteration. For example, a target temperature for non-ablative thermal alteration may be greater than body temperature (e.g., about 37° C.) but less than about 45° C., while a target temperature for ablative thermal alteration may be greater than about 45° C. Exposure to thermal energy between about body temperature and about 45° C. may induce non-ablative thermal alteration via moderate heating of target neural fibers or of vascular or luminal structures that perfuse the target neural fibers. In cases where vascular or luminal structures are affected, the target neural fibers may be denied perfusion, resulting in necrosis of the neural tissue. For example, this may induce non-ablative thermal alteration in the fibers or structures. Exposure to thermal energy greater than about 45° C. (e.g., greater than about 60° C.) may induce thermal ablation via substantial heating of target neural fibers or of vascular or luminal structures that perfuse the target fibers. For example, such higher temperatures may thermally ablate the target neural fibers or the vascular structures that perfuse the target fibers. In some patients, it may be desirable to achieve temperatures that thermally ablate the target neural fibers or the vascular or luminal structures, but that are less than about 90° C., e.g., less than about 85° C., less than about 80° C., or less than about 75° C. Other embodiments can include heating tissue to a variety of other suitable temperatures.

In some embodiments, gastrointestinal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical(s), for example, can be selected to affect the treatment location generally or to selectively affect some structures at the treatment location over other structures. For example, the chemical(s) can be guanethidine, ethanol, phenol, vincristine, a neurotoxin, or another suitable agent selected to alter, damage, or disrupt nerves. In some embodiments, energy (e.g., light, ultrasound, or another suitable type of energy) can be used to activate the chemical(s) and/or to cause the chemical(s) to become more bioavailable. A variety of suitable techniques can be used to deliver chemicals to tissue at a treatment location. For example, chemicals can be delivered via one or more devices, such as needles originating outside the body or within the vasculature or delivery pumps (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., micro-needles) that can be retracted or otherwise blocked prior to deployment. In other embodiments, a chemical can be introduced into tissue at a treatment location via simple diffusion through a vessel or duct wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

In some embodiments, a treatment procedure can include applying a suitable treatment modality at a treatment location in a testing step followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate to the treatment location are suitable for modulation. Performing a testing step can be particularly useful for treatment procedures in which targeted nerves are closely associated with nerves that could cause undesirable side effects if modulated during a subsequent treatment step.

III. Methods for Treatment of Gastrointestinal Conditions

Imbalances of sympathetic and/or parasympathetic neural activity in gastrointestinal organs can cause or exacerbate gastrointestinal conditions, e.g., inflammatory bowel disease, gastrointestinal dysmotility, maldigestion, other chronic inflammatory diseases of the gastrointestinal tract, and other gastrointestinal conditions. As noted previously, disclosed herein are several embodiments of methods directed to treatment of IBD, gastric motility disorders, and other gastrointestinal conditions, as well as conditions associated with imbalances of sympathetic and/or parasympathetic activity in the gastrointestinal organs and/or conditions associated with imbalances of central sympathetic and/or parasympathetic activity, using gastrointestinal neuromodulation. The methods disclosed herein may possess various advantages over a number of conventional approaches and techniques in that they allow for the potential targeting of elevated sympathetic and/or parasympathetic drive, which may either be a cause of IBD, gastric motility disorders, and other gastrointestinal conditions or a key mediator of the multiple manifestations of these conditions. Also, the disclosed methods provide for localized treatment and limited duration treatment regimens, thereby reducing patient long-term treatment compliance issues. With regard to IBD, the methods disclosed herein can be used both to treat acute flares, for maintenance therapy, and to prevent or suppress future flares.

In certain embodiments, the methods provided herein comprise performing gastrointestinal neuromodulation, thereby decreasing sympathetic and/or parasympathetic gastrointestinal nerve activity. Gastrointestinal neuromodulation may be repeated one or more times at various intervals until a desired sympathetic or parasympathetic nerve activity level or another therapeutic benchmark is reached. In one embodiment, for example, a decrease in sympathetic nerve activity may be observed via a marker of sympathetic nerve activity such as plasma norepinephrine (noradrenaline) in IBD patients. Other measures or markers of sympathetic nerve activity can include muscle sympathetic nerve activity (MSNA), norepinephrine spillover, and/or heart rate variability.

In certain embodiments of the methods provided herein, gastrointestinal neuromodulation is expected to result in a change in sympathetic or parasympathetic nerve activity over a specific timeframe. For example, in certain of these embodiments, sympathetic or parasympathetic nerve activity levels are changed over an extended timeframe, e.g., within about 1 month, 2 months, 3 months, 6 months, 9 months or 12 months post-neuromodulation.

In several embodiments, the methods disclosed herein may comprise an additional step of measuring sympathetic or parasympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline nerve activity level is derived from the subject undergoing treatment. For example, baseline nerve activity level may be measured in the subject at one or more timepoints prior to treatment. A baseline nerve activity value may represent sympathetic or parasympathetic nerve activity at a specific timepoint before neuromodulation, or it may represent an average activity level at two or more timepoints prior to neuromodulation. In certain embodiments, the baseline value is based on nerve activity immediately prior to treatment (e.g., after the subject has already been catheterized). Alternatively, a baseline value may be derived from a standard value for nerve activity observed across the population as a whole or across a particular subpopulation. In certain embodiments, post-neuromodulation nerve activity levels are measured in extended timeframes post-neuromodulation, e.g., 3 months, 6 months or 12 months post-neuromodulation.

In certain embodiments of the methods provided herein, the methods are designed to change sympathetic or parasympathetic nerve activity to a target level. In these embodiments, the methods include a step of measuring nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target nerve activity level is reached. In other embodiments, the methods are simply designed to decrease nerve activity below a baseline level without requiring a particular target activity level.

Gastrointestinal neuromodulation may be performed on a patient diagnosed with a gastrointestinal condition such as IBD or a gastric motility disorder to reduce or prevent an increase in one or more measurable physiological parameters corresponding to the condition. In some embodiments where gastrointestinal neuromodulation is used in a patient diagnosed with IBD, for example, gastrointestinal neuromodulation may prevent an increase in, maintain, or reduce the occurrence or severity of abdominal pain, vomiting, or diarrhea. A reduction in a physiological parameter associated with a gastrointestinal condition may be determined by qualitative or quantitative analysis before and after (e.g., 1, 3, 6, or 12 months after) a gastrointestinal neuromodulation procedure.

As discussed previously, the progression of IBD, gastric motility disorders, and other gastrointestinal conditions may be related to sympathetic overactivity and, correspondingly, the degree of sympathoexcitation in a patient may be related to the severity of the clinical presentation of the IBD, gastric motility disorders, and other gastrointestinal conditions. The gastrointestinal system may be positioned to be both a cause (via afferent nerve fibers) and a target (via efferent sympathetic nerves) of elevated central sympathetic drive. In some embodiments, gastrointestinal neuromodulation can be used to reduce central sympathetic drive in a patient diagnosed with a gastrointestinal condition in a manner that treats the patient for the gastrointestinal condition. In some embodiments, for example, MSNA can be reduced by at least about 10% in the patient within about three months after at least partially inhibiting sympathetic neural activity in nerves proximate a gastrointestinal artery innervating a gastrointestinal organ. Similarly, in some instances gastrointestinal norepinephrine spillover to plasma can be reduced at least about 20% in the patient within about three months after at least partially inhibiting sympathetic neural activity in nerves proximate a gastrointestinal artery innervating a gastrointestinal organ. Additionally, measured gastrointestinal norepinephrine content (e.g., assessed in real-time via intravascular blood collection techniques) can be reduced (e.g., by at least about 5%, 10%, or by at least 20%) in the patient within about three months after at least partially inhibiting sympathetic neural activity in nerves proximate a gastrointestinal artery innervating a gastrointestinal organ.

In one prophetic example, a patient diagnosed with IBD can be subjected to a baseline assessment indicating a first set of measurable parameters corresponding to IBD. Such parameters can include, for example, frequency or level of abdominal pain or frequency of vomiting or diarrhea. Following baseline assessment, the patient is subjected to a gastrointestinal neuromodulation procedure. Such a procedure can, for example, include any of the treatment modalities described herein or another treatment modality in accordance with the present technology. The treatment can be performed on nerves proximate the superior mesenteric artery, the inferior mesenteric artery, the superior mesenteric vein, the inferior mesenteric vein, and/or another portion of a vessel or duct of a gastrointestinal organ. Following the treatment (e.g., 1, 3, 6, or 12 months after treatment), the patient can be subjected to a follow-up assessment. The follow-up assessment can indicate a measurable improvement in one or more physiological parameters corresponding to IBD. Additionally, one could measure the dose of immunosuppressant and immune modulating drugs required for maintenance therapy both before and after a gastrointestinal neuromodulation procedure, with a reduction in medications being deemed as a marker of successful therapy.

The methods described herein address the sympathetic excess that is thought to be an underlying cause of IBD, gastric motility disorders, and other gastrointestinal conditions or a central mechanism through which these gastrointestinal conditions manifest their multiple deleterious effects on patients. In contrast, known therapies currently prescribed for IBD, gastric motility disorders, and other gastrointestinal conditions typically address only specific manifestations of these conditions. Additionally, these known therapies can have significant limitations including limited efficacy, and frequently require the patient to remain compliant with the treatment regimen over time. In contrast, gastrointestinal neuromodulation can be a one-time treatment that would be expected to have durable benefits to inhibit the long-term disease progression and thereby achieve a favorable patient outcome. Unlike pharmacologic treatments such as immune modulating agents that affect the entire body, it could also be a more targeted therapy, preferentially affecting the gastrointestinal system.

In some embodiments, patients diagnosed with a gastrointestinal condition can be treated with gastrointestinal neuromodulation alone. However, in other embodiments patients diagnosed with IBD, gastric motility disorders, and other gastrointestinal conditions can be treated with combinations of therapies for treating both primary causative modes of these conditions as well as sequelae of these conditions. For example, combinations of therapies can be tailored based on specific manifestations of the disease in a particular patient.

Treatment of a gastrointestinal condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

IV. Selected Examples of Gastrointestinal Neuromodulation Systems and Devices

Figure 3:
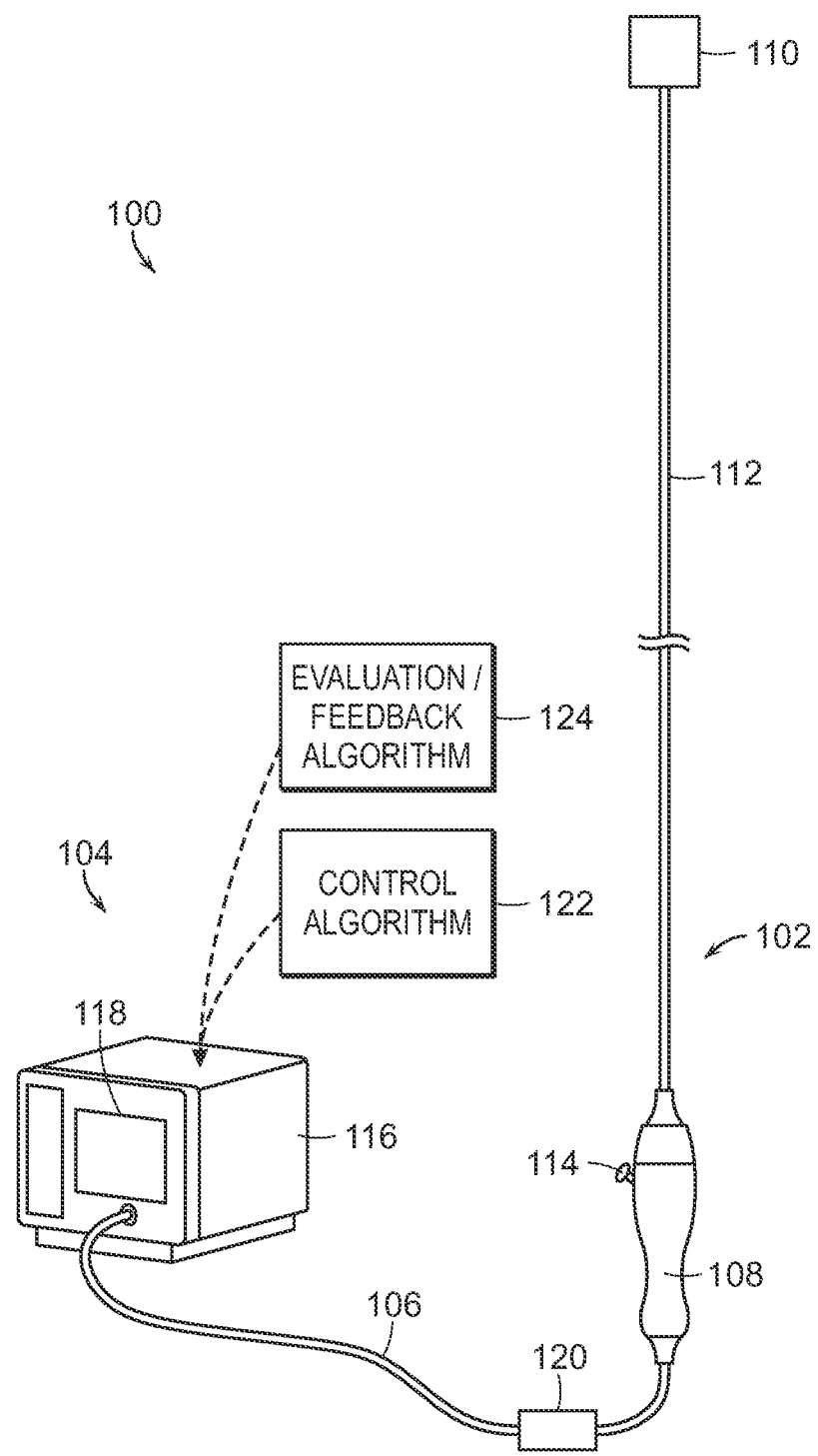
FIG. 3 illustrates an intravascular neuromodulation system configured in accordance with an embodiment of the present technology.

FIG. 3 is a partially schematic diagram illustrating a gastrointestinal neuromodulation system 100 ("system 100") configured in accordance with an embodiment of the present technology. The system 100 can include a treatment device 102, an energy source or console 104 (e.g., an RF energy generator, a cryotherapy console, etc.), and a cable 106 extending between the treatment device 102 and the console 104. The treatment device 102 can include a handle 108, a neuromodulation assembly 110, and an elongated shaft 112 extending between the handle 108 and the neuromodulation assembly 110. The shaft 112 can be configured to locate the neuromodulation assembly 110 intravascularly or intraluminally at a treatment location (e.g., in or near the superior mesenteric artery, the inferior mesenteric artery, the superior mesenteric vein, the inferior mesenteric vein, another portion of a vessel or duct of a gastrointestinal organ, and/or another suitable structure), and the neuromodulation assembly 110 can be configured to provide or support therapeutically-effective neuromodulation at the treatment location. In some embodiments, the shaft 112 and the neuromodulation assembly 110 can be 3, 4, 5, 6, or 7 French or another suitable size. Furthermore, the shaft 112 and the neuromodulation assembly 110 can be partially or fully radiopaque and/or can include radiopaque markers corresponding to measurements, e.g., every 5 cm.

Intravascular delivery can include percutaneously inserting a guide wire (not shown) within the vasculature and moving the shaft 112 and the neuromodulation assembly 110 along the guide wire until the neuromodulation assembly 110 reaches the treatment location. For example, the shaft 112 and the neuromodulation assembly 110 can include a guide-wire lumen (not shown) configured to receive the guide wire in an over-the-wire (OTW) or rapid-exchange configuration (RX). Other body lumens (e.g., ducts or internal chambers) can be treated, for example, by non-percutaneously passing the shaft 112 and neuromodulation assembly 110 through externally accessible passages of the body or other suitable methods. In some embodiments, a distal end of the neuromodulation assembly 110 can terminate in an atraumatic rounded tip or cap (not shown). The treatment device 102 can also be a steerable or non-steerable catheter device (e.g., a guide catheter) configured for use without a guide wire.

The neuromodulation assembly 110 can have a single state or configuration, or it can be convertible between a plurality of states or configurations. For example, the neuromodulation assembly 110 can be configured to be delivered to the treatment location in a delivery state and to provide or support therapeutically-effective neuromodulation in a deployed state. In these and other embodiments, the neuromodulation assembly 110 can have different sizes and/or shapes in the delivery and deployed states. For example, the neuromodulation assembly 110 can have a low-profile configuration in the delivery state and an expanded configuration in the deployed state. In another example, the neuromodulation assembly 110 can be configured to deflect into contact with a vessel wall in a delivery state. The neuromodulation assembly 110 can be converted (e.g., placed or transformed) between the delivery and deployed states via remote actuation, e.g., using an actuator 114 of the handle 108. The actuator 114 can include a knob, a pin, a lever, a button, a dial, or another suitable control component. In other embodiments, the neuromodulation assembly 110 can be transformed between the delivery and deployed states using other suitable mechanisms or techniques.

In some embodiments, the neuromodulation assembly 110 can include an elongated member (not shown) that can be configured to curve (e.g., arch) in the deployed state, e.g., in response to movement of the actuator 114. For example, the elongated member can be at least partially helical/spiral in the deployed state. In other embodiments, the neuromodulation assembly 110 can include a balloon (not shown) that can be configured to be at least partially inflated in the deployed state. An elongated member, for example, can be well suited for carrying one or more heating elements, electrodes, or transducers and for delivering direct heat, electrode-based, or transducer-based treatment. A balloon, for example, can be well suited for containing refrigerant (e.g., during or shortly after liquid-to-gas phase change) and for delivering cryotherapeutic treatment. A balloon can also be used in some embodiments for carrying suitable RF conducting electrodes. In some embodiments, the neuromodulation assembly 110 can be configured for intravascular, transvascular, intraluminal, and/or transluminal delivery of chemicals. For example, the neuromodulation assembly 110 can include one or more openings (not shown), and chemicals (e.g., drugs or other agents) can be deliverable through the openings. For transvascular and transluminal delivery, the neuromodulation assembly 110 can include one or more needles (not shown) (e.g., retractable needles) and the openings can be at end portions of the needles.

The console 104 is configured to control, monitor, supply, or otherwise support operation of the treatment device 102. In some embodiments, the console 104 can be separate from and in communication with the treatment device 102. In other embodiments, the console 104 can be contained within or be a component of the treatment device 102. In still further embodiments, the treatment device 102 can be self-contained and/or otherwise configured for operation without connection to the console 104. As shown in FIG. 3, the console 104 can include a primary housing 116 having a display 118. The system 100 can include a control device 120 along the cable 106 configured to initiate, terminate, and/or adjust operation of the treatment device 102 directly and/or via the console 104. In other embodiments, the system 100 can include another suitable control mechanism. For example, the control device 120 can be incorporated into the handle 108. The console 104 can be configured to execute an automated control algorithm 122 and/or to receive control instructions from an operator. Furthermore, the console 104 can be configured to provide feedback to an operator before, during, and/or after a treatment procedure via the display 118 and/or an evaluation/feedback algorithm 124. In some embodiments, the console 104 can include a processing device (not shown) having processing circuitry, e.g., a microprocessor. The processing device can be configured to execute stored instructions relating to the control algorithm 122 and/or the evaluation/feedback algorithm 124. Furthermore, the console 104 can be configured to communicate with the treatment device 102, e.g., via the cable 106. For example, the neuromodulation assembly 110 of the treatment device 102 can include a sensor (not shown) (e.g., a recording electrode, a temperature sensor, a pressure sensor, or a flow rate sensor) and a sensor lead (not shown) (e.g., an electrical lead or a pressure lead) configured to carry a signal from the sensor to the handle 108. The cable 106 can be configured to carry the signal from the handle 108 to the console 104.

The console 104 can have different configurations depending on the treatment modality of the treatment device 102. For example, when the treatment device 102 is configured for electrode-based or transducer-based treatment, the console 104 can include an energy generator (not shown) configured to generate RF energy, pulsed RF energy, microwave energy, optical energy, focused ultrasound energy (e.g., intravascularly delivered ultrasound, extracorporeal ultrasound, HIFU), magnetic energy, direct heat energy, or another suitable type of energy. In some embodiments, the console 104 can include an RF generator operably coupled to one or more electrodes (not shown) of the neuromodulation assembly 110.

When the treatment device 102 is configured for cryotherapeutic treatment, the console 104 can include a refrigerant reservoir (not shown) and can be configured to supply the treatment device 102 with refrigerant, e.g., pressurized refrigerant in liquid or substantially liquid phase. Similarly, when the treatment device 102 is configured for chemical-based treatment, the console 104 can include a chemical reservoir (not shown) and can be configured to supply the treatment device 102 with one or more chemicals. In some embodiments, the treatment device 102 can include an adapter (not shown) (e.g., a luer lock) configured to be operably coupled to a syringe (not shown). The adapter can be fluidly connected to a lumen (not shown) of the treatment device 102, and the syringe can be used, for example, to manually deliver one or more chemicals to the treatment location, to withdraw material from the treatment location, to inflate a balloon (not shown) of the neuromodulation assembly 110, to deflate a balloon of the neuromodulation assembly 110, or for another suitable purpose. In other embodiments, the console 104 can have other suitable configurations.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

V. Selected Examples of Treatment Procedures for Gastrointestinal Neuromodulation Referring back to FIGS. 1B and 2B, in some embodiments the shaft 22 or 32 and the therapeutic element 24 or 34 can be portions of a treatment device at least partially corresponding to the treatment device 102 shown in FIG. 3. The therapeutic element 24 or 34, for example, can be configured to radially expand into a deployed state at the treatment location. In the deployed state, the therapeutic element 24 or 34 can be configured to contact an inner wall of a vessel and to form a suitable lesion or pattern of lesions without the need for repositioning. For example, the therapeutic element 24 or 34 can be configured to form a single lesion or a series of lesions, e.g., overlapping or non-overlapping. In some embodiments, the lesion or pattern of lesions can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the therapeutic element 24 or 34 can be configured to form a partially-circumferential lesion or a fully-circumferential lesion at a single longitudinal segment or zone of the vessel. During treatment, the therapeutic element 24 or 34 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the therapeutic element 24 or 34 can be configured to cause therapeutically-effective neuromodulation (e.g., using ultrasound energy) without contacting a vessel wall.

A variety of other suitable treatment locations are also possible in and around the superior mesenteric artery 20, the inferior mesenteric artery 30, the superior mesenteric vein, the inferior mesenteric vein, other portions of vessels or ducts of gastrointestinal organs, and/or other suitable structures. For example, in some cases, it can be more convenient to treat the superior mesenteric artery 20 or the inferior mesenteric artery 30 at their trunks, where they meet the aorta. The superior mesenteric artery typically arises from the aorta just below the celiac trunk, and typically supplies blood to the head of the pancreas, duodenum, jejunum, ileum, appendix, cecum, ascending colon, and transverse colon. The inferior mesenteric artery typically arises from the aorta significantly below the superior mesenteric artery, and typically supplies blood to the descending colon, sigmoid colon, and rectum. In both cases, autonomic innervation likely follows the blood supply. In certain embodiments, either the superior or inferior mesenteric artery may be targeted as a treatment location based on the organ or structure associated with the gastrointestinal condition being treated. For example, where gastrointestinal neuromodulation is being used to treat a condition associated with the colon, the treatment location may include the inferior mesenteric artery.

Furthermore, a treatment procedure can include treatment at any suitable number of treatment locations, e.g., a single treatment location, two treatment locations, or more than two treatment locations. In some embodiments, different treatment locations can correspond to different portions of the superior mesenteric artery 20, the inferior mesenteric artery 30, the superior mesenteric vein, the inferior mesenteric vein, other portions of vessels or ducts of gastrointestinal organs, and/or other suitable structures proximate tissue having relatively high concentrations of gastrointestinal nerves. In certain embodiments, different treatment locations may be located in entirely different vessels. For example, treatment locations may be located in the superior and/or inferior mesenteric arteries and also in one or more additional vessels or tissues. The shaft 22 or 32 can be steerable (e.g., via one or more pull wires, a steerable guide or sheath catheter, etc.) and can be configured to move the therapeutic element 24 or 34 between treatment locations. At each treatment location, the therapeutic element 24 or 34 can be activated to cause modulation of nerves proximate the treatment location. Activating the therapeutic element 24 or 34 can include, for example, heating, cooling, stimulating, or applying another suitable treatment modality at the treatment location. Activating the therapeutic element 24 or 34 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the therapeutic element 24 or 34 can be configured to introduce (e.g., inject) a chemical (e.g., a drug or another agent) into target tissue at the treatment location. Such chemicals or agents can be applied at various concentrations depending on treatment location and the relative depth of the target nerves.

Both the superior and inferior mesenteric arteries branch from the abdominal aorta, so the least invasive access route for the therapeutic element 24 or 34 to be positioned at a treatment location within the mesenteric arteries would typically be through femoral, brachial, or radial access to the aorta. As such, in certain embodiments the therapeutic element 24 can be positioned at a treatment location within the superior mesenteric artery 20 via a catheterization path including a femoral, radial, or brachial artery and the aorta. However, other suitable catheterization paths may be used. Catheterization can be guided, for example, using imaging, e.g., magnetic resonance, computed tomography, fluoroscopy, ultrasound, intravascular ultrasound, optical coherence tomography, or another suitable imaging modality. The therapeutic element can be configured to accommodate the anatomy of the superior mesenteric artery 20, the inferior mesenteric artery 30, the superior mesenteric vein, the inferior mesenteric vein, another portion of a vessel or duct of a gastrointestinal organ, and/or another suitable structure. For example, the therapeutic element can include a balloon (not shown) configured to inflate to a size generally corresponding to the internal size of the superior mesenteric artery 20, the inferior mesenteric artery 30, the superior mesenteric vein, the inferior mesenteric vein, another portion of a vessel or duct of a gastrointestinal organ, and/or another suitable structure. In some embodiments, the therapeutic element 24 or 34 can be an implantable device and a treatment procedure can include locating the therapeutic element 24 or 34 at the treatment location using the shaft 22 or 32, fixing the therapeutic element 24 or 34 at the treatment location, separating the therapeutic element 24 or 34 from the shaft 22 or 32, and withdrawing the shaft 22 or 32. Other treatment procedures for modulation of gastrointestinal nerves in accordance with embodiments of the present technology are also possible.

As mentioned previously, the methods disclosed herein may use a variety of suitable energy modalities, including RF energy, microwave energy, laser energy, optical energy, ultrasound energy (e.g., intravascularly delivered ultrasound, extracorporeal ultrasound, HIFU), magnetic energy, direct heat, cryotherapy, or a combination thereof. Alternatively or in addition to these techniques, the methods may utilize one or more non-ablative neuromodulatory techniques. For example, the methods may utilize non-ablative SNS denervation by removal of target nerves, injection of target nerves with a destructive drug or pharmaceutical compound, or treatment of the target nerves with non-ablative energy modalities. In certain embodiments, the amount of reduction of the sympathetic nerve activity may vary depending on the specific technique being used.

In one example, the treatment device 102 set forth in FIG. 3 can be an RF energy emitting device and RF energy can be delivered through energy delivery elements or electrodes to one or more locations along the inner wall of a first gastrointestinal blood vessel (e.g., a mesenteric artery or vein) for predetermined periods of time (e.g., 120 seconds). An objective of a treatment may be, for example, to heat tissue to a desired depth (e.g., at least about 3 mm) to a temperature (e.g., about 65° C.) that would modulate one or more nerve fibers associated with or adjacent to one or more lesions formed in the vessel wall. A clinical objective of the procedure typically is to neuromodulate a sufficient number of gastrointestinal nerves (efferent and/or afferent nerves) to cause a reduction in sympathetic tone or drive to one or more gastrointestinal organs without, for example, disrupting gastrointestinal function and while minimizing vessel trauma. If the objective is met (e.g., tissue is heated to about 65° C. to a depth of about 3 mm) the probability of modulating gastrointestinal nerve tissue (e.g., altering nerve function) is high. In some embodiments, a single neuromodulation treatment procedure can provide for sufficient modulation of target sympathetic nerves (e.g., modulation of a sufficient number of nerve fibers) to provide a desired clinical outcome. In other embodiments, more than one treatment may be beneficial for modulating a desired number or volume of target nerve fibers, and thereby achieving clinical success. In other embodiments, an objective may include reducing or eliminating gastrointestinal nerve function completely.

In a specific example of using RF energy for gastrointestinal nerve modulation, a clinician can commence treatment, which causes the control algorithm 122 (FIG. 3) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time, i.e., in a linear manner. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment, $P_{MAX}$ is 10 watts, or in further embodiment, $P_{MAX}$ is 6.5 watts. In some embodiments, $P_{MAX}$ can be about 6 watts to about 10 watts. Optionally, the power may be maintained at the maximum power $P_{MAX}$ for a desired period of time or up to the desired total treatment time (e.g., up to about 120 seconds), or until a specified temperature is reached or maintained for a specified time period.

In another specific example, the treatment device 102 in FIG. 3 can be a cryogenic device and cryogenic cooling can be applied for one or more cycles (e.g., for 30 second increments, 60 second increments, 90 second increments, etc.) in one or more locations along the circumference and/or length of the first gastrointestinal blood vessel. The cooling cycles can be, for example, fixed periods or can be fully or partially dependent on detected temperatures (e.g., temperatures detected by a thermocouple (not shown) of the neuromodulation assembly 110). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

The neuromodulation assembly 110 can then be located at a second target site in or near a second gastrointestinal blood vessel (e.g., a mesenteric artery or vein), and correct positioning of the assembly 110 can be determined. In selected embodiments, a contrast material can be delivered distally beyond the neuromodulation assembly 110 and fluoroscopy and/or other suitable imaging techniques can be used to locate the second gastrointestinal vessel. The method continues by applying targeted heat or cold to effectuate gastrointestinal neuromodulation at the second target site to cause partial or full denervation of the gastrointestinal organ associated with the second target site.

After providing the therapeutically-effective neuromodulation energy (e.g., cryogenic cooling, RF energy, ultrasound energy, etc.), the method may also include determining whether the neuromodulation therapeutically treated a gastrointestinal condition, a condition associated with sympathetic and/or parasympathetic activity in a gastrointestinal organ, or a condition associated with central sympathetic and/or parasympathetic activity or otherwise sufficiently modulated nerves or other neural structures proximate the first and second target sites. For example, the process of determining whether the neuromodulation therapeutically treated the nerves can include determining whether nerves were sufficiently modulated or otherwise disrupted to reduce, suppress, inhibit, block or otherwise affect the afferent and/or efferent gastrointestinal signals (e.g., by evaluation of suitable biomarkers, stimulation and recording of nerve signals, etc.). In a further embodiment, patient assessment could be performed at time intervals (e.g., 1 month, 3 months, 6 months, 12 months) following neuromodulation treatment. For example, the patient can be assessed for measurements of perceived abdominal pain, vomiting, or diarrhea or for measurements of sympathetic activity (e.g., MSNA, norepinephrine spillover to plasma, whole body norepinephrine spillover, and heart rate variability).

In other embodiments, various steps in the method can be modified, omitted, and/or additional steps may be added. In further embodiments, the method can have a delay between applying therapeutically-effective neuromodulation energy at a first target site at or near a first gastrointestinal blood vessel and applying therapeutically-effective neuromodulation energy at a second target site at or near a second gastrointestinal blood vessel. For example, neuromodulation of the first gastrointestinal blood vessel can take place at a first treatment session, and neuromodulation of the second gastrointestinal blood vessel can take place at a second treatment session at a later time.

As discussed previously, treatment procedures for modulation of gastrointestinal nerves in accordance with embodiments of the present technology are expected to improve at least one condition associated with a gastrointestinal condition and/or with sympathetic or parasympathetic activity in a gastrointestinal organ or a condition associated with central sympathetic and/or parasympathetic activity. For example, with respect to IBD, modulation of gastrointestinal nerves in accordance with embodiments of the present technology is expected to reduce, maintain, or prevent an increase in abdominal pain, vomiting, or diarrhea. With respect to imbalances in central sympathetic activity (e.g., overactivity or hyperactivity), for example, modulation of gastrointestinal nerves is expected to reduce MSNA and/or whole body norepinephrine spillover in patients. These and other clinical effects are expected to be detectable immediately after a treatment procedure or after a delay, e.g., of 1, 2, or 3 months. In some embodiments, it may be useful to repeat gastrointestinal neuromodulation at the same treatment location or a different treatment location after a suitable delay, e.g., 1, 2, or 3 years. In still other embodiments, however, other suitable treatment regimens or techniques may be used.

VI. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with immune system neuromodulation.

A. The Sympathetic Nervous System

The SNS is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up- and down-regulation of many homeostatic mechanisms in living organisms. Fibers from the SNS innervate tissues in almost every organ system, providing at least some regulatory function to physiological features as diverse as pupil diameter, gut motility, and urinary output. This response is also known as the sympathoadrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

1. The Sympathetic Chain

Figure 4:
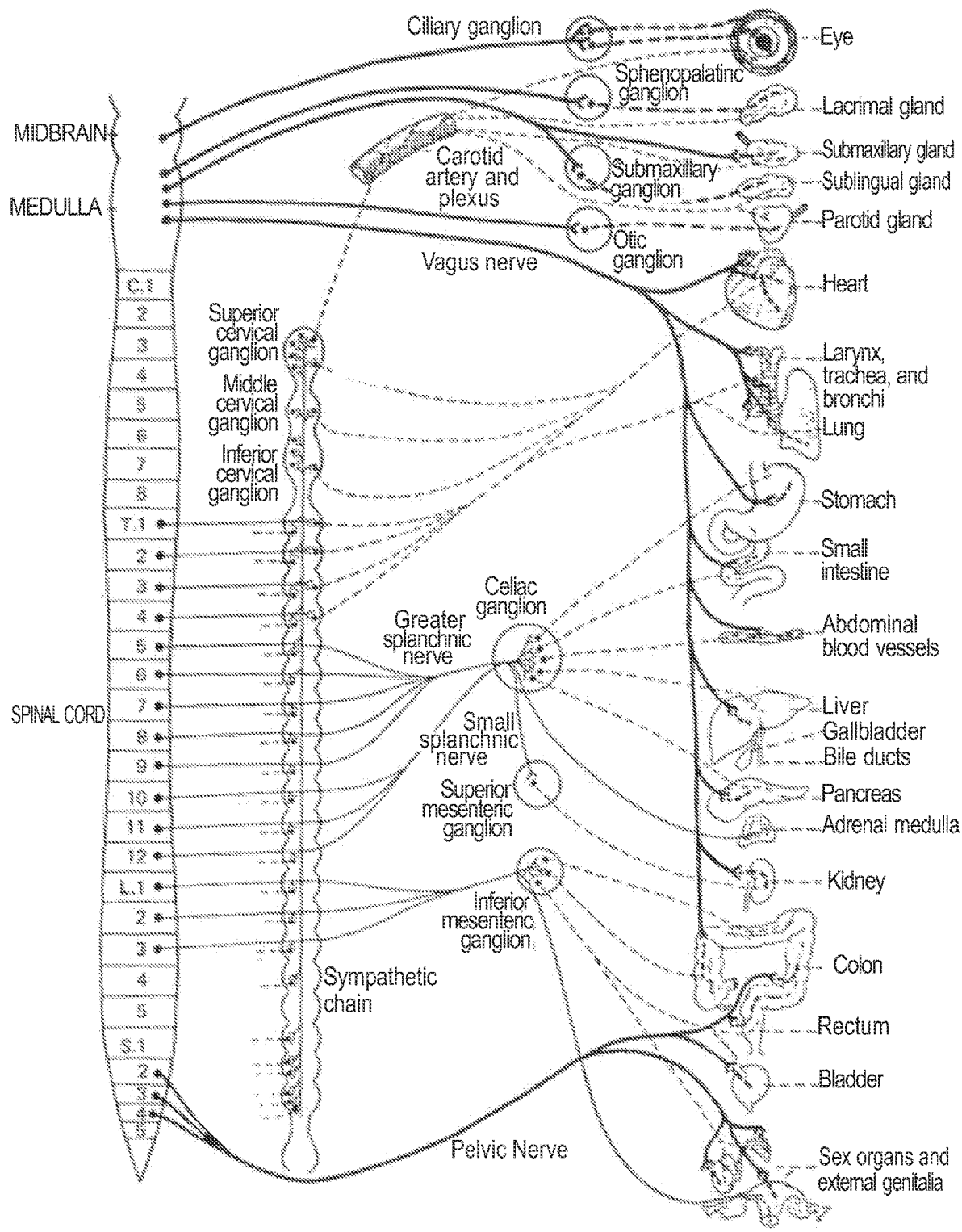
FIG. 4 is a conceptual illustration of the SNS and how the brain communicates with the body via the SNS.

As shown in FIG. 4, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axons relay their message to a second cell through synaptic transmission. The first cell (the presynaptic cell) sends a neurotransmitter across the synaptic cleft (the space between the axon terminal of the first cell and the dendrite of the second cell) where it activates the second cell (the postsynaptic cell). The message is then propagated to the final destination.

In the SNS and other neuronal networks of the peripheral nervous system, these synapses are located at sites called ganglia, discussed above. The cell that sends its fiber to a ganglion is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

FURTHER EXAMPLES

1. A method of treating a human patient diagnosed with a gastrointestinal condition, the method comprising:
   intravascularly positioning a neuromodulation assembly within a gastrointestinal blood vessel of the patient and adjacent to a target gastrointestinal nerve of the patient; and
   reducing sympathetic neural activity in the patient by delivering energy to the gastrointestinal nerve via the neuromodulation assembly to modulate a function of the gastrointestinal nerve,
   wherein reducing sympathetic neural activity improves a measurable physiological parameter corresponding to the gastrointestinal condition of the patient.

2. The method of example 1 wherein the gastrointestinal condition is inflammatory bowel disorder or a gastric motility disorder.

3. The method of example 2 wherein the inflammatory bowel disorder is selected from the group consisting of Crohn's disease, ulcerative colitis, collagenous colitis, lymphocytic colitis, ischaemic colitis, diversion colitis, and Behcet's disease and where the gastric motility disorder is irritable bowel syndrome.

4. The method of any one of examples 1-3 wherein reducing sympathetic neural activity in the patient in a manner that improves a measurable physiological parameter corresponding to the gastrointestinal condition comprises reducing muscle sympathetic nerve activity in the patient.

5. The method of any one of examples 1-3 wherein reducing sympathetic neural activity in the patient in a manner that improves a measurable physiological parameter corresponding to the gastrointestinal condition comprises reducing whole body norepinephrine spillover in the patient.

6. The method of any one of examples 1-5 wherein intravascularly positioning a neuromodulation assembly within a gastrointestinal blood vessel comprises positioning the neuromodulation assembly in at least one of the superior mesenteric artery, the inferior mesenteric artery, the superior mesenteric vein, and the inferior mesenteric vein.

7. The method of any one of examples 1-6 wherein reducing sympathetic neural activity in the patient by delivering energy to the gastrointestinal nerve comprises at least partially inhibiting afferent neural activity.

8. The method of any one of examples 1-6 wherein reducing sympathetic neural activity in the patient by delivering energy to the gastrointestinal nerve comprises at least partially inhibiting efferent neural activity.

9. The method of any one of examples 1-8 wherein reducing sympathetic neural activity in the patient by delivering energy to the gastrointestinal nerve comprises partially ablating the target gastrointestinal nerve.

10. The method of any one of examples 1-9 wherein reducing sympathetic neural activity in the patient by delivering energy to the gastrointestinal nerve via the neuromodulation assembly comprises delivering an energy field to the target gastrointestinal nerve via the neuromodulation assembly.

11. The method of example 10 wherein delivering an energy field to the target gastrointestinal nerve comprises delivering radio frequency (RF) energy via the neuromodulation assembly.

12. The method of example 10 wherein delivering an energy field to the target gastrointestinal nerve comprises delivering ultrasound energy via the neuromodulation assembly.

13. The method of example 12 wherein delivering ultrasound energy comprises delivering high intensity focused ultrasound energy via the neuromodulation assembly.

14. The method of example 10 wherein delivering an energy field to the target gastrointestinal nerve comprises delivering laser energy via the neuromodulation assembly.

15. The method of example 10 wherein delivering an energy field to the target gastrointestinal nerve comprises delivering microwave energy via the neuromodulation assembly.

16. The method of any one of examples 1-15, further comprising removing the neuromodulation assembly from the patient after delivering energy to the gastrointestinal nerve via the neuromodulation assembly to modulate a function of the gastrointestinal nerve.

17. A method, comprising:
   percutaneously introducing a neuromodulation assembly at a distal portion of a treatment device proximate to neural fibers innervating a gastrointestinal organ of a human subject diagnosed with a gastrointestinal condition;
   partially disrupting function of the neural fibers via the neuromodulation assembly; and
   removing the neuromodulation assembly from the subject after treatment,
   wherein partial disruption of the function of the neural fibers therapeutically treats one or more symptoms associated with the gastrointestinal condition of the subject.

18. The method of example 17 wherein partially disrupting function of the neural fibers via the neuromodulation assembly comprises delivering a chemical agent to tissue at a treatment location proximate the neural fibers in a manner that modulates sympathetic neural activity of the neural fibers.

19. The method of example 17 wherein partially disrupting function of the neural fibers via the neuromodulation assembly comprises thermally modulating the neural fibers via at least one wall-contact electrode.

20. The method of example 17 wherein partially disrupting function of the neural fibers via the neuromodulation assembly comprises thermally modulating the neural fibers via a multi-electrode array positioned within a gastrointestinal blood vessel of the patient.

21. The method of example 17 wherein partially disrupting function of the neural fibers via the neuromodulation assembly comprises cryotherapeutically cooling the neural fibers via the neuromodulation assembly.

22. A device for carrying out the method of any of examples 1-21.

CONCLUSION

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while steps may be presented in a given order, alternative embodiments may perform steps in a different order. The various embodiments described herein and elements thereof may also be combined to provide further embodiments. In some cases, well-known structures and functions have not been shown or described in detail to avoid unnecessarily obscuring the description of embodiments of the present technology.

Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout the disclosure to mean including at least the recited feature(s) such that any greater number of the same feature(s) and/or additional types of other features are not precluded. It will also be appreciated that various modifications may be made to the described embodiments without deviating from the present technology. Further, while advantages associated with certain embodiments of the present technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

We claim:

1. A method of treating a human patient diagnosed with obesity and a gastrointestinal hormone imbalance, the method comprising:
   intravascularly positioning a neuromodulation assembly within a gastrointestinal blood vessel of the patient and adjacent to a target gastrointestinal nerve of the patient;
   reducing sympathetic neural activity in the patient by delivering energy to the target gastrointestinal nerve via the neuromodulation assembly; and
   removing the neuromodulation assembly from the patient after delivering energy to the target gastrointestinal nerve,
   wherein reducing sympathetic neural activity results in an improvement in a gastrointestinal hormone level in the patient diagnosed with obesity and the gastrointestinal hormone imbalance following treatment and after removing the neuromodulation assembly from the patient.

2. The method of claim 1 wherein reducing sympathetic neural activity in the patient further comprises reducing muscle sympathetic nerve activity in the patient.

3. The method of claim 1 wherein reducing sympathetic neural activity in the patient further comprises reducing whole body norepinephrine spillover in the patient.

4. The method of claim 1 wherein intravascularly positioning a neuromodulation assembly within a gastrointestinal blood vessel comprises positioning the neuromodulation assembly in at least one of the superior mesenteric artery, the inferior mesenteric artery, the superior mesenteric vein, the inferior mesenteric vein, and a blood vessel or duct of the patient's stomach.

5. The method of claim 1 wherein reducing sympathetic neural activity in the patient by delivering energy to the target gastrointestinal nerve comprises at least partially inhibiting afferent neural activity.

6. The method of claim 1 wherein reducing sympathetic neural activity in the patient by delivering energy to the target gastrointestinal nerve comprises at least partially inhibiting efferent neural activity.

7. The method of claim 1 wherein reducing sympathetic neural activity in the patient by delivering energy to the target gastrointestinal nerve comprises partially ablating the target gastrointestinal nerve.

8. The method of claim 1 wherein reducing sympathetic neural activity in the patient by delivering energy to the target gastrointestinal nerve via the neuromodulation assembly comprises delivering an energy field to the target gastrointestinal nerve via the neuromodulation assembly.

9. The method of claim 8 wherein delivering an energy field to the target gastrointestinal nerve comprises delivering at least one of radio frequency energy, ultrasound energy, high intensity ultrasound energy, laser energy, and microwave energy via the neuromodulation assembly.

10. The method of claim 1 wherein the improvement in the gastrointestinal hormone level results in a reduction in body weight of the patient.

11. The method of claim 1 wherein the improvement in the gastrointestinal hormone level in the patient is detectable within 3 months of delivering energy to the target gastrointestinal nerve.

12. The method of claim 1 wherein the improvement in the gastrointestinal hormone level is detectable within 6 months of delivering energy to the target gastrointestinal nerve.

13. The method of claim 1 wherein the improvement in the gastrointestinal hormone level results in a decrease in gastric motility of the patient.

14. The method of claim 1 wherein reducing sympathetic neural activity in the patient by delivering energy to the target gastrointestinal nerve via the neuromodulation assembly further causes a reduction in an amount of medication taken by the patient.

15. A method of treating an obese human subject having a diagnosed gastrointestinal hormone imbalance, the method comprising:
    intravascularly positioning a neuromodulation assembly at a distal portion of a catheter within a gastrointestinal artery and adjacent to target gastrointestinal nerves of the obese subject, wherein the neuromodulation assembly comprises a plurality of electrodes arranged along an elongated member;
    transforming the neuromodulation assembly from a low-profile, delivery state to a deployed state tending to have a helical shape to position the electrodes in apposition with an inner wall of the gastrointestinal artery; and
    at least partially ablating the target gastrointestinal nerves via electrical energy from the electrodes positioned along the gastrointestinal artery,
    wherein at least partially ablating the target gastrointestinal nerves therapeutically causes a reduction in the body weight of the obese subject having the diagnosed gastrointestinal hormone imbalance.

16. The method of claim 15 wherein intravascularly positioning a neuromodulation assembly at a distal portion of a catheter within a gastrointestinal artery comprises positioning the neuromodulation assembly within at least one of (a) the superior mesenteric artery of the obese subject or a branch thereof, (b) the inferior mesenteric artery of the obese subject or a branch thereof, and (c) a blood vessel or duct of the obese subject's stomach.

* * * * *